US011548966B2

(12) United States Patent
Chisholm (10) Patent No.: US 11,548,966 B2
(45) Date of Patent: Jan. 10, 2023

(54) HARDENABLE MULTI-PART ACRYLIC COMPOSITION (71) Applicant: Lucite International Specialty Polymers and Resins Limited, Billingham (GB)

(72) Inventor: Michael Stephen Chisholm, Newton Aycliffe Durham (GB)

(73) Assignee: Lucite International Specialty Polymers and Resins Limited, Billingham (GB)

(*) Notice: Subject to any disclaimer, the term of this patent is extended or adjusted under 35 U.S.C. 154(b) by 17 days.

(21) Appl. No.: 16/763,502

(22) PCT Filed: Nov. 20, 2018

(86) PCT No.: PCT/GB2018/053350
§ 371 (c)(1),
(2) Date: May 12, 2020

(87) PCT Pub. No.: WO2019/097263
PCT Pub. Date: May 23, 2019

(65) Prior Publication Data
US 2020/0338231 A1  Oct. 29, 2020

(30) Foreign Application Priority Data

Nov. 20, 2017 (GB) .................................. 1719227

(51) Int. Cl.
*C08F 265/06* (2006.01)
*A61L 24/06* (2006.01)
(Continued)

(52) U.S. Cl.
CPC ........ *C08F 265/06* (2013.01); *A61K 49/0404* (2013.01); *A61L 24/001* (2013.01);
(Continued)

(58) Field of Classification Search
None
See application file for complete search history.

(56) References Cited

U.S. PATENT DOCUMENTS 4,268,639 A * 5/1981 Seidel ..................... A61L 24/06
525/303
10,022,307 B2 * 7/2018 Chisholm ............. C08F 265/06
(Continued)

FOREIGN PATENT DOCUMENTS

CN        1350005 A     5/2002
CN      104926974 A     9/2015
(Continued)

OTHER PUBLICATIONS

Bryan T. H. Koh et al. "Effect of storage temperature and equilibration time on polymethyl methacrylate (PMMA) bone cement polymerization in joint replacement surgery." Journal of Orthopaedic Surgery and Research, vol. 10:178, 2015, pp. 1-6. (Year: 2015).*
(Continued)

*Primary Examiner* — Isaac Shomer
(74) *Attorney, Agent, or Firm* — Myers Bigel, P.A.

(57) ABSTRACT

The invention relates to a hardenable multi-part acrylic composition. The composition has at least two parts which react with each other upon being mixed together to progressively harden to form a solid cement, such as a bone cement. The beads in the first part comprise an acrylic bead polymer core produced by suspension polymerisation and having a Tg of >70° C. and emulsion polymerised acrylic microparticles at least partially coating the surface of the acrylic bead polymer core. The microparticles may form a porous coalesced network. The bone cement composition comprises the first part and a liquid second part and optionally, further parts. The parts are operable to form a cement which hardens to a solid mass upon mixing of the parts together. The composition further comprises an acrylic monomer compo-
(Continued)

nent in the second part and an initiator component. A method of production of coated beads for the hardenable multipart composition and a solid cement is also described.

21 Claims, 2 Drawing Sheets

(51) Int. Cl.
| | | |
|---|---|---|
| *C08L 33/12* | (2006.01) | |
| *A61K 49/04* | (2006.01) | |
| *A61L 24/00* | (2006.01) | |
| *C08K 3/22* | (2006.01) | |

(52) U.S. Cl.
CPC ....... *A61L 24/0015* (2013.01); *A61L 24/0036* (2013.01); *A61L 24/06* (2013.01); *C08K 3/22* (2013.01); *C08L 33/12* (2013.01); *C08K 2003/2244* (2013.01); *C08L 2207/53* (2013.01)

(56) References Cited

U.S. PATENT DOCUMENTS

| | | | |
|---|---|---|---|
| 10,149,919 B2* | 12/2018 | Chisholm | A61K 6/889 |
| 10,155,066 B2* | 12/2018 | Chisholm | C09J 4/06 |
| 2011/0263739 A1* | 10/2011 | Chisholm | A61L 24/0094 521/149 |
| 2015/0051603 A1* | 2/2015 | Chisholm | C08F 265/06 606/94 |
| 2015/0361317 A1* | 12/2015 | Janowicz | C08G 18/10 428/355 AC |
| 2016/0279289 A1 | 9/2016 | Chisholm et al. | |

FOREIGN PATENT DOCUMENTS

| | | | |
|---|---|---|---|
| CN | 105592866 A | 5/2016 | |
| WO | 2010/018412 | 2/2010 | |
| WO | 2013/144590 | 10/2013 | |
| WO | 2015/044688 | 4/2015 | |
| WO | 2015/044689 | 4/2015 | |
| WO | 2015044689 A1 | 4/2015 | |
| WO | WO-2015044688 A1 * | 4/2015 | ............. A61L 24/06 |

OTHER PUBLICATIONS

Stanford University Chemical Engineering. "Chemical Engineering 160/260 Polymer Science and Engineering Lecture 13: Polymerization Techniques." https://web.stanford.edu/class/cheme160/lectures/lecture13.pdf accessed by examiner on May 11, 2022, 18 pages. (Year: 2022).*

International Preliminary Report on Patentability corresponding to International Application No. PCT/GB2018/053350 dated May 26, 2020.

International Search Report and Written Opinion corresponding to International Application No. PCT/GB2018/053350 dated Feb. 27, 2019.

Search Report corresponding to Application No. GB1719227.9 dated May 22, 2018.

V.L.Dimonie, et al, "Emulsion Polymerization and Emulsion Polymers", P.A. Lovell and M.S. El-Aasser, Eds, John Wiley & Sons Ltd, Chapter 9, pp. 294-326, (1997).

"Office Action corresponding to Chinese Application No. 2018300870256 dated Dec. 14, 2021".

* cited by examiner

HARDENABLE MULTI-PART ACRYLIC COMPOSITION

CROSS REFERENCE TO RELATED APPLICATIONS

This application is a § 371 national phase application of PCT Application No. PCT/GB2018/053350, filed on Nov. 20, 2018, which claims priority to British Application No. 1719227.9 filed on Nov. 20, 2017, the entire contents of each of which is incorporated by reference herein.

The present invention relates to a hardenable multi-part acrylic composition, in particular but not exclusively, an acrylic composition which has at least two parts which react with each other upon being mixed together to progressively harden to form a solid cement, such as a bone cement.

Hardenable compositions formed by mixing together acrylic polymers and monomers are useful in a wide range of applications. Particular utility is found in dental, medical, adhesive and construction applications, where such materials have been used for over 40 years.

Dental applications include denture bases, denture base plates, denture liners, denture repairs, custom trays, veneering for crowns and bridgework, artificial teeth, veneers and repair for natural teeth and tooth restorative fillings. Medical applications include bone cements for bone cavities such as prosthetic cements, cranial cements and vertebral cements in vertebroplasty and kyphoplasty. Further applications include the production of shaped articles that harden extra-corporeally and which can then be introduced into the body.

Typical hardenable acrylic compositions are generally composed of two components. The first, usually solid, component comprises polymer particles and, if appropriate, further additives, such as polymerisation initiators and catalysts, fillers and dyestuffs. The second component comprises a liquid monomer or monomers and further additives, such as accelerators/activators and stabilisers. When ready for use, the two components are mixed together to form a liquid or semi-solid paste, which, under the action of the polymerisation initiators and accelerators/activators, gradually increases in viscosity and hardens into a solid.

The first component typically used consists of small spherical beads (usually about 20-150 microns in diameter) of poly(methyl methacrylate) (PMMA) and a small amount of polymerisation initiator such as dibenzoyl peroxide (BPO), usually encapsulated within the PMMA bead, but which can also be added as a separate component. The second component is usually a monomer, typically methyl methacrylate (MMA), which may also contain a polymerisation accelerator such as N,N-dimethyl-p-toluidine (a tertiary amine) (DMPT) and an inhibitor such as hydroquinone (HQ) to prevent the monomer from spontaneously polymerising.

When the two components are mixed together, the polymer particles are wetted with monomer, solvated and begin to dissolve. The solvated polymer particles release dibenzoyl peroxide initiator into the monomer which interacts with accelerator, if present, to produce radicals that react with the monomer and initiate room temperature addition polymerisation of the monomer. The mixture starts out at a relatively low viscosity and progresses to a stiffer and stiffer system that eventually hardens completely to a solid cement or cement-like consistency.

Compositions hardenable to a solid at room temperature (so-called "self-curing" or "cold-curing" systems) have dough times that are typically 4 to 10 minutes and set times that are typically 10 to 25 minutes in duration. The work time effectively defines the time period available for the operator to manipulate the dough in the desired fashion, for example pressing into a denture mould for denture base manufacture, or pressing into a bone cavity during hip repair or replacement or injecting into a vertebral cavity during spinal surgery or forcing into a gap or cavity during industrial cementing operations. The dough time is determined by the rate at which the combination of solid and liquid components rise in viscosity immediately after mixing and is controlled by a number of factors, such as polymer bead particle size and shape, polymer molecular weight, and polymer composition.

WO2010018412 discloses a hardenable two part acrylic composition wherein the solid part comprises acrylic polymer particles formed of a network of coalesced emulsion polymerized acrylic microparticles and, optionally, acrylic polymer beads mixed therewith. Although an improvement in work time is disclosed it is generally necessary to utilize two different solid particles which both require preparation and isolation.

It is one object of the present invention to address this problem. It is clearly advantageous to provide a hardenable two part acrylic composition which has a reduced dough time. In addition, a simplified manufacturing process would be more efficient and reliable providing further advantages to both the manufacturer and end user.

According to a first aspect of the present invention there is provided coated acrylic polymer beads comprising:
  a) an acrylic bead polymer core produced by suspension polymerisation and having a Tg of >70° C.; and
  b) emulsion polymerised acrylic microparticles at least partially coating the surface of the said acrylic bead polymer core.

Preferably, at least 1% of the bead polymer core surface is coated with the said microparticles, more typically, at least 2%, most typically, at least 5%. In particularly preferred embodiments, the bead polymer core surface may have a higher proportion of its surface coated with said microparticles, for example, at least 10%, at least 20%, at least 30%, or at least 40% of the surface is coated with said microparticles.

The coated acrylic polymer beads according to the first aspect of the invention are of particular use in the production of hardenable multi-part acrylic compositions.

Therefore according to a second aspect of the invention there is provided a hardenable multi-part acrylic composition comprising a first part and a liquid second part and optionally, further parts, the parts being operable to form a cement which hardens to a solid mass upon mixing of the parts together, the composition further comprising an acrylic monomer component in the second part, an initiator component, the initiator component being present in an amount effective to polymerize the monomer component upon being mixed and/or activated therewith, and optionally, a radiopacifying filler, characterized in that the first part comprises coated acrylic polymer beads according to the first aspect or further coated acrylic polymer bead aspects of the present invention.

It has surprisingly been found that by at least partially coating the acrylic beads with emulsion polymerised acrylic microparticles, the coated beads have an increased work time and shorter dough time thus allowing the user, often a surgeon, to have more time to use the dough in a workable state.

Preferably at least 50% of the coated acrylic polymer beads in the composition have a surface which is at least 1% coated with the said microparticles, more typically, at least 2%, most typically, at least 5% such as at least 10%, at least 20%, at least 30%, or at least 40%.

More preferably at least 60%, at least 70%, or at least 80% of the coated acrylic polymer beads have a surface which is at least 1%, at least 2% or at least 5% coated with the said microparticles, such as at least 10%, at least 20%, at least 30%, or at least 40%

A proportion of the emulsion polymerized microparticles present in the composition may not form part of the at least partial coating of the acrylic bead polymer core, i.e. a proportion of the microparticles may be present as clusters of microparticles and/or as individual microparticles. For the avoidance of doubt, any free emulsion polymerized microparticles or clusters of microparticles which do not coat the acrylic bead polymer cores may not be considered to be themselves coated acrylic polymer beads of the first aspect and, if present, merely make up part of the balance of total polymer present in the acrylic polymer composition of the second aspect.

Preferably at least 1% by weight of the emulsion polymerized acrylic microparticles present in the composition of the second aspect are present in the surface coating of the acrylic bead polymer cores, more typically, at least 2% by weight, at least 5% by weight or at least 10% by weight. In particularly preferred embodiments, 10%-90% by weight or more preferably 20%-75% by weight of the emulsion polymerized acrylic microparticles present in the composition are present in the at least partial coating of the surface of the acrylic bead polymer cores.

The microparticles coated onto the said bead polymer core surface may take any suitable form such as discrete particles or a coalesced or partly coalesced monolayer of particles on the core surface or agglomerated microparticles. Additional monolayers of particles may coalesce on the bead polymer core surface to form a plurality of microparticle layers.

Preferably, in the case of agglomerated microparticles, the coated microparticles form a microporous mass of microparticles on the surface of the core.

In certain embodiments of the invention, the acrylic coated polymer beads of the first aspect or the first part of the composition of the second aspect is a solid component or is or forms part of a solid part.

By isolating the coated acrylic polymer beads prior to providing the hardenable multi-part acrylic composition, it is possible to use the advantageous coated beads in a solid/liquid hardenable multi-part acrylic composition as well as a liquid/liquid hardenable multi-part acrylic composition. Furthermore, it is not necessary to separately blend two separate solid powders because the surface coated beads already include the required solid components. Still further, by coating the bead, preferential dissolution of the polymer type in the liquid monomer may be achieved, i.e. the emulsion polymerized microparticles prevent or retard dissolution of the bead polymer whilst the emulsion microparticle is itself dissolved thereby providing an unique degree of control over the dissolution of the respective original polymer particles. Still further the coating of the emulsion microparticles onto the bead polymer core hinders complete formation of a larger particle formed from a network of emulsion polymerized microparticles thus providing more accessible emulsion polymerized microparticles spread over the surface of the bead core than those that are, for example, spray dried separately.

In other embodiments of the invention the acrylic coated polymer beads of the first aspect are provided in a liquid phase or the first part of the second aspect is a liquid part.

A liquid first part is advantageous in that the mixing of a liquid/liquid composition is generally more convenient for the user than the mixing of a solid/liquid composition. The liquid may be a suspension resulting from the coating of the beads without further separation or it may be produced following separation and re-suspension.

Surprisingly, it has been possible to produce coated beads in an advantageous manner.

According to a further aspect of the present invention there is provided a method of production of coated beads for a hardenable multi-part composition comprising the steps of:
a) preparing polymer bead particles by suspension polymerization to form a suspension of suspension polymerised bead particles;
b) preparing polymer emulsion microparticles by emulsion polymerization to form a dispersion of emulsion polymerized microparticles;
c) mixing the suspension of a) and dispersion of b) in the presence of an electrolyte to effect coagulation of the emulsion microparticles with the bead particles to form an acrylic bead polymer core at least partially coated with emulsion polymerised acrylic microparticles.

Advantageously, the production of the coated particles can utilize the liquid phase present as a result of the polymerization processes of a) and/or b). Accordingly, separate drying and processing of the beads and/or emulsion microparticles is not necessarily required. Optionally, the coated beads can be separated and dried and used as a dry powder or utilized in the resulting liquid phase directly or separated and dried and re-suspended in a new liquid phase and utilized thereafter.

Accordingly, the method of production of the coated beads may comprise the sequential steps of preparing a, typically aqueous, suspension of polymer bead particles by suspension polymerisation, preparing a dispersion of polymer emulsion microparticles by emulsion polymerisation, mixing the bead particle suspension with the emulsion microparticle dispersion in the presence of an electrolyte, heating the mixture with stirring to effect electrostatically controlled coagulation of the polymer emulsion microparticles in the presence of the polymer beads, optionally cooling the mixture and then either isolating the mixture of polymer particles produced as a solid powder optionally by dewatering, washing and drying or, alternatively, the coated polymer bead particles produced may be retained as a suspension, typically in water, without the requirement to isolate the particles in a dry form. The volume of the bead particle suspension is generally larger than the volume of emulsion microparticle dispersion to be mixed therewith so that generally the emulsion microparticle dispersion is added to the bead particle suspension either together with the electrolyte or separately therefrom. Typically the ratio of emulsion microparticle dispersion to bead particle suspension is between 2:98 to 60:40 w/w thereof, more preferably, 4:96 to 50:50 w/w, most preferably, 6:94 to 40:60 w/w. However, other ratios are also possible.

There is no particular limitation on the temperature of the mixture of polymer bead particles and polymer emulsion microparticles in step c). It is usually in the range of 0° C. to 100° C., preferably in the range 40-95° C.

Typically, the continuous phase for the suspension polymerisation is water. Typically, the continuous phase for the emulsion polymerisation is water. Typically, the bead polymer core produced by the methods of the invention has a Tg of >70° C.

In any aspect, the Tg of the core is preferably, >75° C., more typically, >80° C., most typically, >85° C.

The electrolyte which can be used in the present invention is not particularly limited as long as it is capable of coagulating the emulsion polymerized microparticles in the polymer bead suspension. Suitable electrolytes may be sodium chloride, potassium chloride, lithium chloride, sodium bromide, potassium bromide, lithium bromide, potassium iodide, sodium iodide, potassium sulfate, sodium sulfate, ammonium sulfate, ammonium chloride, sodium nitrate, potassium nitrate, calcium chloride, ferrous sulfate, magnesium sulfate, zinc sulfate, copper sulfate, barium chloride, ferrous chloride, ferric chloride, magnesium chloride, ferric sulfate, aluminium sulfate, potassium alum, iron alum, sodium acetate, calcium acetate, sodium formate, calcium formate and mixtures thereof.

Preferred electrolytes are sodium chloride, potassium chloride, sodium sulfate, ammonium chloride, calcium chloride, magnesium chloride, magnesium sulfate, barium chloride, ferrous chloride, aluminium sulfate, potassium alum and iron alum.

The electrolyte may be added to the suspension of polymer beads and/or emulsion polymerised microparticles in solid form or as a pre-dissolved solution in water.

The concentration of the electrolyte in the mixture, which is typically an aqueous mixture, of polymer beads and emulsion polymerised microparticles is generally at least 0.01 wt %, preferably at least 1.0 wt % or more preferably at least 2.0 wt %.

The first part of the second aspect of the present invention comprises polymer particles and, if appropriate, further additives, in addition to polymerisation initiators such as catalysts, fillers, radiopacifiers and dyestuffs. The liquid second component of the present invention comprises a liquid monomer or monomers and further additives, such as accelerators/activators and stabilisers. When ready for use, the two components are mixed together to form a liquid or semi-solid paste, which, under the action of the polymerisation initiators and accelerators/activators, increases in viscosity and hardens into a solid.

As indicated, the composition may include more than two parts, for instance the initiator component and/or any of the further additives could be stored in a separate third part but for convenience the multi-part acrylic composition of any of the aspects of the invention herein is typically only a two-part composition, i.e. there is no third or further part.

The acrylic composition first part and liquid second part are preferably stored and reacted between 0 and 30° C., more preferably, between 18 to 25° C., most preferably, between 20 to 23° C. and in any case typically under normal atmospheric pressure ranges. The preparation of a cement from the mixing of the acrylic composition first part and the liquid second part can be carried out in various ways that will be appreciated by those skilled in the art, for example by hand mixing.

Typically, the initiator component is present in an amount effective to fully polymerize the monomer component. For example, to polymerize at least 85% w/w of the monomer component, more typically, at least 90% w/w, most typically, 95%-98% w/w of the monomer component. In addition, the initiator component may be present in excess of the amount that would be effective to fully polymerize the monomer component.

The radiopacifying filler may optionally be present in the coated acrylic polymer beads or the emulsion polymerized acrylic microparticles of the first or second aspect, or in another part of the composition of the second aspect.

Preferably, at least 90% w/w of the total acrylic monomer component in the composition is present in the liquid second part, more preferably, at least 95% w/w, most preferably, at least 99% w/w. In preferred embodiments, substantially all the acrylic monomer component in the composition is present in the liquid second part. Typically, therefore, the acrylic monomer component is present in only one part of the composition. Typically, the acrylic monomer component containing liquid part includes acrylic polymer particles dissolved therein.

Typically, the said acrylic monomer component and the said initiator component are located in separate parts of the said multi-part composition so that the part containing the monomer component is storage stable to polymerization.

The invention extends in another aspect to a solid cement composition produced from mixing a multi-part acrylic composition according to any of the aspects herein.

Advantageously, the invention is for use in the treatment of human or animal bone, generally as a replacement thereof and/or as a cement.

Furthermore, the invention extends in another aspect to coated acrylic polymer beads of the first or further coated acrylic polymer bead aspects for use as a dough time reduction agent or as a mechanical strength improver in a hardenable multi-part acrylic composition.

According to a further aspect of the present invention there is provided a method of producing an acrylic cement from a multi-part acrylic composition according to the second aspect of the present invention comprising the step of mixing the said first, second and optionally further parts.

The above mixing process may be by any suitable means, for example a manual mixing process.

The method of producing an acrylic cement from a multi-part acrylic composition according to the second aspect of the invention may comprise the following steps:
a) mixing the acrylic composition first part with the liquid second part to make a dough;
b) optionally, placing the dough in a mould or body cavity or around an implant by hand manipulation or injection; and
c) allowing the dough to set and harden to a solid mass.

As indicated, the composition includes emulsion polymerized microparticles. These may be made in accordance with techniques known to those skilled in the art.

The acrylic polymer particles are, as separate components, typically, in the presence of suitable other composition additives known to the skilled person. Such composition additives include initiators, catalysts, dyestuffs and fillers.

A further advantage is that the hardenable compositions formed from the invention also display a long working time thereby providing a longer time period for the operator to manipulate the cement dough in the desired fashion during application.

An advantage of the coated acrylic polymer beads of the invention is the rapid dough time that is reached in the presence of an acrylic monomer composition. However, the working time and set time for the dough need to vary depending on the application. This can be achieved by varying the amount, type and particle size of the acrylic polymer particles. Accordingly, the particle size of both the acrylic polymer beads and the emulsion polymerized microparticles and the amount of emulsion polymerized microparticles present will depend upon the final application and this will be appreciated by the skilled person.

The larger the average particle size of either particle, the longer the working time will be. The skilled person will also appreciate that the molecular weight of the polymer and the presence of accelerators can also influence the working time and the set time. An important aspect of the present invention is therefore the reduced dough time achievable by the presence of the coated acrylic polymer bead particles whereas the invention is not restricted to a particularly reduced or increased working time or set time because this will depend on the application. Typical dough times achievable in the present invention are from 30 secs such as 30 secs to 10 minutes. Accordingly, the invention allows the use of lower viscosity doughs as the dough time is reached at an early point in the polymerization reaction and the working time is therefore lengthened.

The polymerization of at least one acrylic monomer composition to produce an acrylic polymer particle such as the beads or microparticles of the invention may take place with or without excess initiator.

Typically, a preferred embodiment of the hardenable composition of any aspect of the present invention is prepared by:
a) suspension polymerizing an acrylic monomer/polymer syrup in the presence of, and optionally, in the presence of excess, initiator to produce acrylic polymer bead particles;
b) emulsion polymerizing an acrylic monomer composition in the presence of, and optionally, in the presence of excess, initiator to produce a dispersion of emulsion polymerised microparticles;
c) mixing the acrylic polymer bead particles of step a) and the emulsion polymerized microparticles of step b), optionally, with added initiator, in the presence of an electrolyte to form coated acrylic polymer beads, optionally separating the said coated beads, to form a liquid or solid first part respectively;
d) producing a liquid second part containing acrylic monomer and accelerator/activator;

A particularly preferred method introduces an excess of initiator into the suspension polymerization step a) and/or the emulsion polymerization step b) so that residual initiator is encapsulated within the acrylic polymer bead particles and/or the emulsion polymerized microparticles and, therefore, in the coated acrylic polymer beads. However, alternatively, initiator can also be added subsequently to the acrylic polymer composition first part in step c).

When the two parts are mixed together, the coated acrylic polymer beads are wetted with monomer, solvated and begin to dissolve. The emulsion polymerised microparticles on the surface dissolve at a faster rate than the polymer bead cores. The solvated polymer particles release initiator into the monomer which interacts with accelerator, if present, to produce radicals that react with the monomer and initiate room temperature addition polymerization of the monomer. The mixture starts out as a relatively low viscosity cement and progresses to a stiffer and stiffer system that eventually hardens completely to its final set composition.

This constantly changing viscosity of the cement is characterised by dough and set times and maximum exotherm temperature attained, as defined by BS ISO 5833:2002. The dough time is considered to be the length of time following the start of mixing for the cement to achieve a dough-like mass that does not adhere to a gloved finger when gently touched. The set time is considered to be the time taken to reach a temperature midway between ambient and maximum.

The dough and set times and maximum exotherm temperatures are very important parameters that determine how the hardenable compositions are to be used. Compositions hardenable at room temperature (so-called "self-curing" or "cold-curing" systems) have dough times that are typically 4 to 10 minutes and set times that are typically 10 to 25 minutes in duration. These parameters effectively define the time period available for the operator to manipulate the dough in the desired fashion, for example pressing into a denture mould for denture base manufacture, or pressing into a bone cavity during hip repair or replacement or injecting into a vertebral cavity during spinal surgery. It may be advantageous to maximise the working time available to the operator. This should ideally be achieved without an increase in the set time as this defines the end point for the cementing or fixing operation. This therefore focuses attention on shortening the dough time. Therefore, in the present invention typical dough times are as low as 30 secs. Preferably, the dough time is from 30 secs to up to 10 mins such as 9 or 8 mins. The dough time is determined by the rate at which the combination of liquid components rises in viscosity immediately after mixing and is controlled by a number of factors, such as polymer bead particle size and shape, polymer molecular weight, and polymer composition.

Polymer Beads

The acrylic bead polymer cores according to the invention are produced by suspension polymerisation. Such polymer beads are well known to the skilled person in the field of acrylic polymers.

The term beads as used herein is not meant to be interpreted restrictively unless indicated otherwise and refers to a discrete polymer particle of any suitable size, shape and surface texture. Nevertheless, such beads are typically smooth and broadly spherical. In the context of the present application however, the term bead may be used to differentiate this type of acrylic polymer particle from emulsion polymerized microparticles or larger particles formed from coalesced emulsion polymerized microparticles.

The mean particle size of the bead particles whether acrylic bead polymer cores of the invention or uncoated sub-populations of bead particles (as described herein), is preferably, at least 1 µm, such as 2 or 2.5 µm and may, in any case be up to 60, 120 or 180 µm. Typically, the bead particles may be in the range 1-180 µm, more preferably, 2-150 µm, most preferably, 2.5-120 µm.

Generally, herein the average or mean particle size is determined by a technique appropriate to the size of the particle being characterised. For instance, sub-micron particles may be characterised by their Z-average particle size whereas particles >10 µm can be characterised by their mean particle size. Particles between 1 and 10 µm could be characterised by either measurement. Accordingly, herein, emulsion polymerized microparticles are preferably characterised by their Z-average particle size and bead particles are preferably characterised by their mean particle size.

In preferred embodiments, one or more further sub-populations of acrylic polymer particle is present in the multi-part acrylic composition in addition to the population of coated acrylic polymer bead cores. Typically, the further sub-population is an uncoated sub-population of acrylic bead polymer. In any case, the further sub-population of acrylic polymer particles may or may not differ from the coated acrylic polymer bead core and/or emulsion polymerised microparticles in molecular weight (MW), molecular weight distribution, porosity, the nature and distribution of the (co)monomer residues, particle size, particle size distribution, and/or polymer type, the presence or absence of residual initiator and, if present, the amount and type of residual initiator. The further sub-populations of acrylic polymer particles may therefore be of one or more types for example suspension polymerized, emulsion polymerized and/or bulk polymerized. Typically, if suspension polymerized the sub-population(s) are present as polymer beads and if emulsion polymerized the sub-population(s) are present as emulsion polymerized microparticles which may be coalesced together, agglomerated together or independent. Alternatively, the sub-population(s) may be present as crushed, milled, or ground bulk polymerized acrylic polymer or crushed, milled, or ground acrylic bead polymer.

For instance, there may be two, three or four sub-population(s) of acrylic polymer particle. Typically, there is at least one further sub-population of uncoated acrylic bead polymer, preferably in the first part of the composition, particularly in a solid first part therewith. Preferably, where there are sub-population/s of acrylic polymer particles/beads there is at least 1 wt % of each sub-population, more preferably, 5 wt %, most preferably, 10 wt %.

Where there is a sub-population of beads as well as a main population of beads, a smaller particle size sub-population may be in the range 10-90 microns and a larger particle size sub-population may be in the range 50-300 microns with the proviso that the larger particle size sub-population has a higher average particle size than the smaller average particle size sub-population.

Emulsion Polymerized Microparticles

The emulsion polymerized microparticles may be in any suitable form. Typically, the emulsion polymerized microparticles when at least partially coating the polymer beads are in the form of a network of coalesced emulsion polymerized microparticles on the surface of the polymer beads.

For the avoidance of doubt, by coalesced is not meant that the individual microparticles merge completely but that they join together sufficiently to form a network of particles. Typically, the microparticles come into close contact but also retain individual character.

Preferably, the Z-average particle size of the emulsion polymerized microparticles is less than 2 µm as determined by light scattering using a Malvern Zetasizer nano series S particle size analyzer (adding one drop of emulsion to 1 ml of de-ionised water in a measurement cuvette, allowing the test sample to equilibrate at 25° C. and determining Z-average particle size using the software provided by the instrument), more preferably, less than 1 µm most preferably, less than 0.8 µm, especially, less than 0.5 µm. A preferred Z-average particle size range for the emulsion polymerized microparticles is between 0.01-2 µm, more preferably, 0.02-1 µm, most preferably, 0.05-0.5 µm, especially 0.1-0.45 µm, as determined by light scattering using a Malvern Zetasizer as above. In any case, to perform their function, the emulsion polymerized microparticles of the present invention have a smaller particle size/Z-average particle size than the bead polymer core being coated.

Emulsion polymerized microparticles are well known in the field of impact modifiers. For this reason an impact modifier such as butadiene or butyl acrylate is typically introduced as a comonomer into one of the shells of the multistage core shell particle. However, in the hardenable compositions of the present invention, an impact modifier may not be required. Accordingly, the emulsion microparticles of the present invention may be free from impact modifier co-monomer residues.

A core shell (C:S) ratio of the acrylic polymer microparticles is typically, between C:S 95:5% wt and C:S 40:60% wt, more typically, between C:S 90:10% wt and C:S 50:50% wt, preferably, between C:S 85:15% wt and C:S 70:30% wt.

Typically, the emulsion polymerized microparticles may be single stage or multistage i.e. the so called core/shell particles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion polymerized microparticles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulfate) or through using emulsifiers. Once the seed particles are formed, the core and shell are formed from sequential addition of further aliquots of monomer and initiator.

Typically, the emulsion polymerized microparticles are applied to the polymer beads without isolating the microparticles in a dried form, i.e. the emulsion polymerised microparticles are applied to the polymer beads as a dispersion formed from the emulsion polymerisation process.

However, the emulsion polymerized microparticles may be isolated prior to applying the microparticles to the surface of the polymer beads by drying of the liquid emulsion to form a powder.

Preferably the emulsion polymerized microparticles are not isolated in a dry form as this involves a further manufacturing step.

Where the emulsion polymerized microparticles are isolated, the preferred means of drying the emulsion polymerized microparticles is to use spray drying. However, other methods of direct drying of the emulsion polymerized microparticles are also possible e.g., vacuum paddle or rotational drying. These drying techniques and the prior emulsion polymerization allow very careful control of the emulsion polymerized microparticle size which gives easy reproducibility and reduces batch to batch variation.

By drying herein is meant reduction of the moisture content of the relevant solid to <10% w/w, more preferably, <5% w/w, most preferably, <2% w/w.

The % wt solids content of the emulsion before drying or use is typically, between 5 and 60% wt, more typically, between 7.5 and 55% wt, preferably, between 10 and 52.5% wt.

The emulsion polymerized microparticles are typically acrylic polymer microparticles.

As mentioned previously, the invention extends to an additional sub-population of emulsion polymerized acrylic microparticles present in the composition, typically, in the first part thereof, more typically, in a solid first part thereof and most typically as a network of coalesced emulsion polymerized microparticles distinct from those coating the acrylic bead polymer core. Suitably, such a network may be formed by spray drying emulsion polymerized acrylic microparticles.

Coated Polymer Beads

Advantageously, the emulsion polymerized microparticles when coated on the polymer beads form a porous coalesced network, more preferably, a microporous coalesced network.

According to a further aspect of the present invention there is provided coated acrylic polymer beads comprising:
a) an acrylic bead polymer core produced by suspension polymerisation; and
b) emulsion polymerised acrylic microparticles at least partially coating the surface of the said acrylic bead polymer core wherein the microparticles form a porous coalesced network, more preferably, a microporous coalesced network.

The coalescing of the emulsion polymerized microparticles does not cause them to merge completely and instead they form a network of joined microparticles on the surface of the bead. In addition, they may also coalesce onto the surface of the bead as individual microparticles.

By microporous in the present invention is included networks having an average pore size of between 0.1 and 2000 nm, more preferably, between 1-1000 nm, most preferably, 10-500 nm. The extent and degree of surface coating of the coated acrylic polymer beads may be determined by inspection such as SEM inspection. Pore size may be determined by scanning electron microscopy (SEM) according to the following test method: Sprinkle the sample of coated acrylic polymer beads or beads onto a conducting self-adhesive carbon tab on a standard aluminium SEM stub. Coat the sample with a thin layer of metal (Au/Pd) by vacuum metallization to avoid charging in the SEM instrument. SEM images may be taken using a FEI Quanta FEG 250 Environmental SEM using accelerating voltage of 5 kV and working distance of 10 mm. Imaging is carried out on several coated beads or beads and representative images obtained at different magnifications Typically, the network of coalesced emulsion polymerized microparticles coated on the polymer beads has a large surface area resulting at least in part from the presence of voids in said network.

Typically, as mentioned above, for the preferred solid/liquid two-part hardenable composition the emulsion polymerized microparticles are coagulated onto the polymer beads and the coated beads subsequently filtered and dried. Typically, it has been found that emulsion polymerized microparticles can coalesce into a loosely hexagonal close packed matrix generally in the same plane but, in the present case, due to holes and imperfections in this arrangement and also the three dimensional structure of the particulate network, a porous macrostructure results. The emulsion polymerized microparticles are also, inevitably, present in the coalesced network on the polymer beads, in smaller clusters and also as individual microparticles.

Due to the nature of the coalesced network of microparticles on the polymer beads, the microparticles which make up the network are still substantially present.

For the avoidance of doubt, any reference herein to the average particle size of the emulsion polymerized microparticles is with regard to the emulsion polymerized microparticles themselves and not the average particle size of any larger particle formed of a network of coalesced microparticles.

Radiopacifiers

Suitable radiopacifying fillers may be selected from the list comprising zirconium dioxide, strontium carbonate, powdered tantalum, powdered tungsten, barium sulfate and mixtures thereof. Preferably, the radiopacifying filler is barium sulfate.

By radiopacifying herein is meant the ability to render a material more distinguishable from surrounding material when subjected to X-rays.

The radiopacifying filler may be added to any or both parts of the composition. Optionally, however, at least some of the radiopacifying filler may be encapsulated within and/or adsorbed on the acrylic polymer particles/beads either the coated beads of the invention or in a sub-population of acrylic particles/beads.

Notwithstanding the above, it is also possible for some or all of the radiopacifying filler to be present in the composition and/or hardened cement in a form that is not encapsulated and/or adsorbed in or on acrylic polymer particles/beads, for example in the liquid second part. This is either independently added radiopacifying filler or radiopacifying filler that has migrated from an encapsulated or adsorbed form into the surrounding liquid.

The radiopacifying filler may be encapsulated within and/or adsorbed on the acrylic polymer microparticles and/or the acrylic polymer beads. Optionally however, the radiopacifying filler is encapsulated within and/or adsorbed on the polymer beads, more preferably, a sub-population of uncoated bead polymer.

Typically, the level of radiopacifying filler in the hardenable multi-part composition of the invention is between 1 and 50% w/w, more typically, between 5 and 40% w/w most typically, between 6.5 and 30% w/w.

Polymer and Other Component Amounts

Typically, the coated acrylic polymer beads together with any uncoated acrylic polymer beads form at least 98% w/w of the undissolved polymer present in the composition of the invention prior to monomer mixing, more preferably, at least 99% w/w, most preferably, approximately 100% w/w of the undissolved polymer present in the composition prior to mixing. The ratio of coated and uncoated acrylic polymer beads when present is typically in the ratio 5:1 to 1:5 w/w. Upon mixing the monomer polymerizes and causes the mixed composition to form a cement which gradually hardens eventually setting to a solid. Some polymer, preferably, acrylic polymer as defined herein may also be dissolved in the monomer composition prior to mixing. Such levels of dissolved polymer are typically in the range 0-60% w/w in the acrylic monomer component, more typically 10-30% w/w.

The coated acrylic polymer beads together with radiopacifying filler may typically form between 50-99.9% w/w of the acrylic polymer composition first part, more preferably, 60-97.5% w/w, most preferably, 65-94.5% w/w. The balance is generally made up of other solids which may be fillers, pigments, dyestuffs, catalysts, and initiator.

The ratio of emulsion polymerized microparticles to suspension polymerized beads varies depending on the final application. Nevertheless, it is advantageous in some applications such as bone cements to have a ratio thereof of between 1:99 to 50:50 w/w thereof, more preferably, 3:97 to 40:60 w/w, most preferably, 5:95 to 30:70 w/w. However, no restriction should be taken hereby and other ratios are also possible.

The liquid second part may include in addition to monomer, other polymer composition components known to the skilled person such as acrylic polymer, dyestuffs, catalysts, accelerators/activators, inhibitors, plasticisers etc. It is more typical to have acrylic monomer as the only liquid carrier in the composition, optionally with acrylic polymer particles dissolved therein and with other components added such as accelerators, inhibitors dyes etc. Generally, the amount of monomer in the hardenable composition, whether in the second, or further part, is in the range 10-70% w/w, more typically 15-60% w/w, more preferably 20-50% w/w. Typically, the monomer is present at these overall compositional levels in the second part.

Typically, the liquid second part does not include dissolved polymer. However, when both monomer and acrylic polymer dissolved resin or particles form the bulk of the second liquid part, or further liquid parts, the ratio of acrylic monomer: polymer is in the range 99:1 to 40:60 w/w.

The acrylic polymer composition first part may be present as a dry powder prior to mixing with the monomer composition. The weight ratio of dry powder component to monomer component is generally <3:1, more preferably, <2.5:1, most preferably, <2.2:1. Typically, the weight ratio is in the range 2.15-1.85:1.

Accelerators/activators may be present in the unmixed composition in the range 0.1 to 5% by mass, more typically, 0.5-3% by mass.

The total level of unreacted initiator, whether residual or added, in the multi-part acrylic composition is typically, 0.1-10% w/w of the acrylic composition, preferably, 0.15-5% w/w, more preferably, 0.2-4.0% w/w.

Where initiator is used in one of the components, this may itself be encapsulated within the polymer bead and/or emulsion polymerized microparticles or separately added to any parts of the composition. Although it is possible to have initiator in the liquid part with the acrylic monomer component such would only have a short shelf life. Accordingly, typically, the initiator and acrylic monomer component are located in separate parts of the composition.

Where polymer is dissolved in monomer in the liquid second part, or any further liquid parts, the polymer must preferably contain very low (e.g. <0.1% w/w) levels of residual initiator to avoid shortening of the shelf life.

The initiator may be present in any of the acrylic polymer particles that form part of the acrylic composition. The initiator in the acrylic polymer particles may be the residual amount of unreacted initiator used in the formation of the polymer particles which is therefore the equivalent of the excess amount of initiator. Some initiator can alternatively or additionally be added as a separate component to the multi-part composition. In the emulsion polymerized microparticles or bead polymer particles whether the coated bead polymer particles or otherwise, the level of residual initiator present before reaction is typically, 0.001-10% w/w polymer particle, preferably, 0.1-6% w/w, more preferably 0.1-5% w/w.

Preferably, the initiator is present at a level which will effect polymerization of the monomer component that is at least greater than 90% polymerization, more typically, greater than 93%, more typically greater than 95% polymerization.

A further polymer component may be present in the liquid second part dissolved or partly dissolved in the acrylic monomer component.

The polymer components are typically in the presence of suitable other polymer composition components known to the skilled person. Such polymer composition additives include initiators, emulsifiers, catalysts, pigments, dyestuffs and fillers.

Specific Materials

Initiators that can be used to initiate the suspension polymerization of the acrylic bead polymer particles and therefore those which may form residual initiators in the composition to initiate the hardening process include: azo compounds, peroxides, peroxyesters and persulfates, specifically azobis(isobutyronitrile), azobis(2-methylbutyronitrile), azobis(2,4-dimethylvaleronitrile), azobis(4-cyanovaleric acid), dilauroyl peroxide, tert-butyl peroxyneodecanoate, dibenzyl peroxide, cumyl peroxide, tert-butylperoxy-2-ethyl hexanoate, tert-butyl peroxydiethyl acetate, tert-butyl peroxy benzoate, tert-butyl hydroperoxide, potassium persulphate, ammonium persulphate and sodium persulphate.

Initiators that can be used to initiate the emulsion polymerization and therefore those which may form residual initiators in the composition to initiate the hardening process are persulfates, (e.g., potassium, sodium or ammonium), peroxides (e.g., hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

In addition to the emulsion initiators above, a particularly preferred initiator for the hardening stage is dibenzoyl peroxide.

Initiators that can be used for conventional or emulsifier free emulsion polymerization and therefore which may be present as residual initiators include:—ionic water-soluble initiators, such as potassium, sodium or ammonium persulfate.

In addition, any one or more of the above initiators can be added to the composition independently.

In a particularly preferred embodiment, the acrylic polymer particles incorporate the initiator in their polymer matrix. The initiator may be incorporated into the polymer matrix of acrylic polymer bead particles and/or emulsion polymerized microparticles. Preferably, the initiator is incorporated in the acrylic polymer bead particles whether coated or uncoated. Accordingly, in this embodiment, the initiator is not added separately to the first part of the composition.

Advantageously, the initiator for the hardenable composition can be added as excess initiator during the polymerization of any of the particles so that some initiator is used in the polymerization of the particles but as the particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerization process and, accordingly, excess initiator is used in the final shell polymerization stage. During polymerization of the polymer particle more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

Preferably, step (b) of the method of production of the invention comprises seed, core and at least one shell emulsion polymerization step. A particularly preferred method introduces an excess of initiator into the emulsion polymerization step so that residual initiator is encapsulated within the emulsion microparticles. Preferably, in a multistage emulsion polymerization, the excess initiator is introduced during the final stage so that it is present in the outer shell of the multistage particle. However, alternatively, initiator can also be added subsequently to the acrylic polymer emulsion.

For the avoidance of doubt, by "excess initiator" is meant, the portion of initiator that is not required to complete polymerisation of the acrylic polymer particles and is available for subsequent reaction after the initial polymerization of the acrylic polymer particles is terminated.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT) in the acrylic monomer composition can also affect the set time. Increased accelerator concentration results in shortened set time.

Typically, herein, initiator will be present in the composition at a level of 0.1 to 5% w/w total monomer and initiator.

In compositions according to the invention other fillers may be used and these will be known to the skilled person in the art of such fields. Additionally, organic x-ray opaque monomers can be used in addition to fillers. These can be copolymerized into any of the acrylic polymer particles during their production or incorporated into the acrylic monomer composition. Typical organic x-ray opaque monomers include halogenated methacrylates or acrylates, e.g., 2,3-dibromopropyl methacrylate or 2-methacryloyloxyethyl-2,3,5-triiodobenzoate. For the avoidance of any doubt, such x-ray opaque monomers are not to be regarded as fillers.

Emulsifiers that can be used in the emulsion polymerization are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxy ethyl)-N-octadecyl sulfosuccinate, sodium salt of sulfated alkylphenol ethoxylates, sodium alkane sulfonate, sodium dodecyl sulfate or sodium 2-ethylhexyl sulfate), nonionic (e.g., polyethylene glycol nonylphenyl ethers, polyethylene oxide octylphenyl ethers, or di-functional ethylene oxide/propylene oxide block copolymers) or cationic emulsifiers (e.g., hexadecyltrimethylammonium bromide or alkyl polyglycoletherammonium methyl chloride). Reactive or polymerisable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethylhexadecyldimethylammonium bromide.

The mixing of the further components of the invention with the liquid carrier in the liquid second part, or any further liquid parts, may be carried out by any suitable technique known to the skilled person for mixing solids or liquids with a liquid.

Preferably, the compressive strength of the solid produced by mixing the said parts in any aspect of the present invention is greater than 40 MPa, more preferably greater than 70 MPa. The typical range of compressive strengths found in the produced solid is 40-130 MPa, more preferably 70-130 MPa.

Definitions

The term "adsorbed" takes its usual meaning and means bound to the surface thereof.

The term "liquid" herein does not require definition because it is well understood by the skilled person. However, for the avoidance of doubt it also includes a flowable material having a liquid carrier such as a slurry, suspension, emulsion or paste that is thus susceptible of delivery through a syringe or caulking gun outlet by the application of pressure. Typically, the term liquid is applicable to the material or composition at least between 5 and 35° C., more typically, between 5 and 30° C.

The term "dispersion" includes suspensions and colloids. Generally, however, the dispersion of polymer emulsion microparticles is a colloidal dispersion thereof and, in any case, is typically, an aqueous dispersion.

The terms "suspension" and "colloid" both mean a non-solvated form.

The term "solid part" means a non-liquid or non-gaseous part and is generally a free flowing dry particulate material usually made up of one or a mixture of powder(s) and not including a liquid carrier.

The liquid components of the composition according to the invention are storage stable. By "storage stable" is meant that the monomer or liquid does not polymerize under normally acceptable storage conditions of temperature and time i.e. between 5 and 30° C. and 1 to 250 days, more typically, 15 to 25° C. and 1 to 170 days.

The term "coated" or "coating" used herein in the context of the relationship between the polymer beads and the polymer microparticles means that at least a single layer of microparticles occludes the surface of the polymer bead in a particular region.

The Z-average particle size herein is determined by light scattering using a Malvern Zetasizer nano series S particle size analyzer.

The mean particle size herein may be determined using a Coulter LS230 laser diffraction instrument.

The term "microparticle" herein is meant a polymer particle having an average particle size of <10 μm, preferably <2 μm, more preferably <1 μm.

By acrylic polymer herein in relation to the coated acrylic polymer bead particles, the emulsion polymerized microparticles, the suspension polymerized bead particles, or otherwise is meant independently for each acrylic polymer component a homopolymer of a polyalkyl(alk)acrylate or (alk) acrylic acid or copolymers of a alkyl(alk)acrylate or (alk) acrylic acid with one or more other vinyl monomers and wherein at least 50% of the monomer residues are acrylic monomer residues, more typically, at least, 70% thereof, most typically, at least 80% thereof, especially, methyl methacrylate residues at such levels. Typically, a homopolymer of methyl methacrylate or a copolymer of methyl methacrylate with one or more other vinyl monomers is used. By other vinyl monomers is included a further alkyl (alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid or acrylic acid; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone or vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate, particularly the compatible acrylic crosslinking monomers. Typically the acrylic polymer of the coated acrylic polymer bead particles, the emulsion polymerized microparticles, or the suspension polymerized bead particles is independently a homopolymer of methyl methacrylate or a copolymer thereof with one or more of the above mentioned vinyl monomers, more preferably, with styrene or methyl acrylate.

Crosslinking monomers can be used to crosslink the acrylic polymer particles. For the emulsion polymerized microparticles, crosslinking may be carried out in the core and the shell, or only the core, or only the shell. Crosslinking serves the purpose of fine-tuning the properties of the hardenable multi-part acrylic composition.

The weight average molecular weight (Mw) of the emulsion polymerized microparticles is typically, between 25,000 daltons and 3,000,000 daltons, more typically, between 100,000 daltons and 1,500,000 daltons, preferably, between 250,000 and 1,000,000, for instance, between 250,000 and 600,000. Molecular weight may be determined for this purpose by gel permeation chromatography (GPC).

Although, the molecular weights of the polymers in the polymer components of the hardenable composition may influence the dough and work times, the invention is not restricted to any particular molecular weight. In any case, reductions in the molecular weight and/or increases in the particle size of the acrylic polymer particles can be used to increase the work time of the hardenable composition.

The weight average molecular weight (Mw) of the bead type of polymer particles, is typically, between 10,000 daltons and 3,000,000 daltons, more typically, between 30,000 daltons and 1,000,000 daltons, preferably, between 50,000 and 700,000, for instance, between 60,000 and 600,000 Daltons. Molecular weight may be determined for this purpose by gel permeation chromatography (GPC).

The term "population" is generally understood by the skilled person but for the avoidance of doubt refers to a plurality of polymer particles having a specific mean particle size, weight average molecular weight, particle size distribution and molecular weight distribution as is usually produced by monomer(s) which have undergone the same polymerization process(es) together and sub-population should be understood as a further population of polymer particles. The weight average molecular weight and particle size of such sub-populations may be in the ranges defined for the acrylic polymer microparticles and coated acrylic polymer bead herein.

By acrylic monomer herein is meant any one or more suitable alkyl(alk)acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate or isobornyl methacrylate; hydroxyl-functional acrylates such as 2-hydroxyethyl methacrylate, hydroxypropylethyl methacrylate, 2-hydroxyethyl acrylate, or hydroxypropyl acrylate; and compatible crosslinking monomers such as allyl methacrylate, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate. Typically, methyl methacrylate is the preferred acrylic monomer, especially for the second part. Other comonomers may be utilized with the acrylic monomers such as vinyl compounds such as styrene, vinyl pyrrolidinone or vinyl pyridine; and other compatible crosslinking monomers such as divinyl benzene. Preferred acrylic comonomers are styrene and methyl acrylate.

The acrylic monomer component of the invention is generally, provided with an accompanying suitable inhibitor such as hydroquinone (HQ), methyl hydroquinone (MeHQ), 2,6-di-tertiary-butyl-4-methoxyphenol (Topanol O) and 2,4-dimethyl-6-tertiary-butyl phenol (Topanol A). The inhibitor is present to prevent the monomer from spontaneously polymerising. A suitable inhibitor is hydroquinone to ensure long shelf life at room temperature.

Polymerization activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for some applications the use of heat in "heat-cure" systems is also possible. For instance, dentures can be activated by heat. When present in the composition, accelerator/activator is typically present at a level that will effectively activate the polymerisation reaction in the presence of initiator, typically, this is at a level of 0.1 to 5% w/w total monomer and accelerator/activator.

By alkyl herein is meant $C_1$-$C_{18}$ alkyl wherein the term alkyl and alk encompasses cycloalkyl and hydroxyl functional $C_1$-$C_{18}$ alkyl. By alk herein is meant $C_0$-$C_8$ alk.

By "acrylic composition" is meant a composition where at least 50% of the total monomer and monomer residues present are present as or derived from one or more of the above defined acrylic monomers, more typically, at least 70%, most typically, 95% or especially, 99% of the total monomer or monomer residues present in the composition.

There is no particular temperature limitation on the use of the present invention. Generally, however it is used at temperatures acceptable to the operator i.e. temperatures found during normal working conditions that may be encountered indoors or outdoors by the operator, for example 5-40° C. and atmospheric pressure and/or applied syringe pressure.

Notwithstanding the foregoing, a particularly advantageous application of the acrylic composition of the aspects of the invention is its use as bone cement compositions. Such compositions are used in arthroplasty and vertebroplasty. A similar application for the compositions of the present invention is dental repairs.

Nevertheless, the advantages of the invention can be seen as generally desirable in many industrial applications and therefore, the invention is not restricted to bone cement and dental applications although these are preferred embodiments.

Emulsion polymerized microparticles are well known in the field of impact modifiers. For this reason an impact modifier such as butadiene or butyl acrylate is typically introduced as a comonomer into one of the shells of the multistage core shell particle. However, in the multi-part compositions of the present invention, an impact modifier may not be required. Accordingly, the emulsion polymerized acrylic polymer microparticles of the present invention may be free from impact modifier co-monomer residues.

The invention extends to a multi-part bone cement or dental cement or building cement or structural adhesive or laminating adhesive or jointing or sealing composition according to any aspects of the present invention.

Preferably, in a bone cement or dental cement composition the components thereof are biocompatible components at least once the composition is set to a solid.

For medical applications such as bone cement and dentistry to which the compositions of the invention are mainly directed the composition is biocompatible and in particular hardens to a solid cement or adhesive that is biocompatible in situ. Accordingly, the composition of the invention finds particularly advantageous utility as a medical implant material such as a bone cement or a solid effective in dental applications. Accordingly, the multi-part composition of the invention is typically a bone cement composition or dental composition.

According to a further aspect of the present invention there is provided a medical implant material produced from mixing a multi-part acrylic composition according to the present invention.

According to a still further aspect of the present invention there is provided a multi-part composition according to any aspects of the present invention for use in surgery, more particularly for use in the treatment of or in association with or in place of human or animal bone or teeth.

According to a still further aspect of the present invention there is provided a multi-part composition according to any aspect of the present invention for use in the replacement or partial replacement of human or animal bone.

According to a still further aspect of the present invention there is provided a multi-part composition according to any aspect of the present invention for use in dentistry, more particularly in the treatment of human teeth or animal teeth or for use in veterinary surgery, more particularly, for use in the treatment of hoof, nail or horn.

According to a still further aspect of the present invention there is provided a multi-part composition according to any aspect of the present invention for use in the replacement or partial replacement of human teeth or animal teeth, hoof, nail or horn.

The hardenable compositions formed from the invention also display a long working time thereby providing a longer time period for the operator to manipulate the cement dough in the desired fashion during application.

Advantageously, the final cured hardened cement composition may be porous. This porosity allows the mechanical properties of the hardenable composition to be matched to those of e.g. vertebral bone, thereby avoiding well known problems associated through implantation of artificial materials that are higher in modulus than the surrounding natural bone.

However, in any case, the formulation of the present invention can also be altered to adjust the level of porosity and vary the mechanical properties, e.g., to achieve mechanical properties that satisfy the requirements of ISO 5833:2002.

A still further advantage of the invention when used as a bone cement is that the control of porosity (size and topography) allows improved control over the controlled release of therapeutic agents such as antibiotics or antifungals into the surrounding bone and tissue.

Porosity as mentioned above is particularly a feature of liquid/liquid compositions.

According to a further aspect of the present invention there is provided a solid cement composition produced from mixing a multi-part acrylic composition according to the any aspect of the present invention which is porous. Typically, the solid cement porosity is adapted for controlled release of one or more therapeutic agents.

The invention extends to a multi-part composition or a first part according to any aspect of the present invention comprising a pharmaceutically effective amount of a therapeutic agent. After mixing the multi-part acrylic composition, implanting and then forming the solid cement composition, the therapeutic agent elutes into the surroundings of the implant to provide a therapeutic, typically, an antimicrobial or antifungal effect.

Suitable therapeutic agents may be selected from the list comprising gentamicin, vancomycin, cefazolin, ciprofloxacin, linezolid, levofloxacin, rifampin, clindamycin and tobramycin. Such therapeutic agents may be used on their own or as mixtures of two or more therapeutic agents. The total amount of therapeutic agent to use is typically 1 to 5 wt % of the total first part.

Preferred compositions of the present invention are cold-cure compositions in other words, a separate heat activation step is not required and the compositions cure upon being mixed together.

In a preferred embodiment, the composition of the present invention includes coated acrylic polymer bead in the first part and uncoated acrylic bead polymer in the first and optionally second parts and initiator in the first part and the second part comprises a solution of initiator-free acrylic polymer (preferably, PMMA) in acrylic monomer (preferably, MMA) with accelerator.

Embodiments of the invention will now be described with reference to the accompanying examples and by reference to the drawings in which.

EXAMPLES

Characterisation Techniques:

The molecular weight was measured by gel permeation chromatography using poly(methyl methacrylate) standards for calibration. Tetrahydrofuran was used as the mobile phase. The weight average molecular weight (Mw), number average molecular weight (Mn) and the polydispersity (Mw/Mn) were measured.

The Z average emulsion particle size was determined using a Malvern Zetasizer nano series S particle size analyser.

The mean particle size of acrylic polymer beads was determined using a Coulter LS230 laser diffraction instrument.

Reduced viscosity (RV, dl/g) was measured in chloroform (1 wt % solution) using an Ubbelohde viscometer type OB at 25° C.

Wt % residual dibenzoyl peroxide content was determined by a titration method.

Wt % water content was determined by a Karl Fischer method using a Metrohm 874 over sample processor with 831 coulometer.

Brookfield viscosity (BV, centipoise (cPs)) of the acrylic emulsions was determined at 25° C. using a Brookfield viscometer model DV-E operating with spindle number 5 and speed 20.

Scanning electron microscopy (SEM) imaging was carried out using a FEI Quanta FEG 250 Environmental SEM. Specimens were prepared for SEM imaging by gently sprinkling the dried polymer powder directly onto conductive carbon sticky tabs mounted on SEM stubs. Any loose material was carefully dislodged and a very thin two pass conductive metal coating (Au/Pd) applied to the samples prior to SEM imaging.

Preparative Example 1

Preparation of 50.1% wt Solids Acrylic Polymer Dispersion (MMA/styrene 85/15 wt % Copolymer)

600 grams of deionised water was added to a five-litre round bottomed glass flask fitted with a nitrogen inlet, condenser and electrically operated stainless steel paddle stirrer. The water was heated to 80° C. by means of a water bath whilst stirring at 150 revolutions per minute (rpm). A flow of nitrogen was passed through the vapour space of the flask above the surface of the liquid.

An emulsified monomer mixture was prepared consisting of 850 grams methyl methacrylate (MMA), 150 grams styrene, 5.0 grams of sodium lauryl sulfate and 300 grams of deionised water. This mixture was stirred for 60 minutes prior to and throughout addition to keep it emulsified.

With the temperature of the water at 80° C., a polymer seed (Stage 1) was prepared by adding 30 grams of the emulsified monomer mixture to the flask followed by 10 millilitres of a 2 wt % solution of potassium persulfate in deionised water. Following a slight exotherm, the reaction proceeded for thirty minutes until the temperature returned to 80° C.

The core was then grown over the polymer seed particles (Stage 2) by firstly adding 10 millilitres of a 2 wt % solution of potassium persulfate in deionised water to the flask followed by continuous addition of 300 grams of the emulsified monomer mixture over approximately 25 minutes using a peristaltic pump. The reaction proceeded for a further 15 minutes after the completion of addition of the monomer mixture until the temperature returned to 80° C. This step was then repeated twice.

30.0 grams of 75% active dibenzoyl peroxide were dissolved in the remaining 370 grams of emulsified monomer mixture with stirring for 45 minutes.

The BPO-containing shell was then grown over the core (Stage 3) by firstly adding 10 millilitres of a 2 wt % solution of potassium persulfate in deionised water to the flask followed by continuous addition of the emulsified monomer mixture containing added BPO over approximately 25 minutes using a peristaltic pump. The reaction proceeded for a further fifteen minutes after all the monomer mixture had been added until the temperature had returned to 80° C.

The resultant acrylic polymer dispersion was then cooled to below 40° C. and filtered through a 150 micron screen.

The acrylic polymer dispersion had a solids content of 50.1% wt, reduced viscosity of 2.72 dl/g, Brookfield viscosity of 130 cPs, residual dibenzoyl peroxide of 2.2 wt % and a z-average dispersion particle size of 254 nm.

Preparative Example 2

Preparation of 25% wt Solids Acrylic Polymer Dispersion (PMMA Homopolymer)

1500 grams of deionised water was added to a five-litre round bottomed glass flask fitted with a nitrogen inlet, condenser and electrically operated stainless steel paddle stirrer. The water was heated to 80° C. by means of a water bath whilst stirring at 150 revolutions per minute (rpm). A flow of nitrogen was passed through the vapour space of the flask above the surface of the liquid.

A monomer mixture was prepared consisting of 500 grams methyl methacrylate, 1.0 gram of 1-dodecanethiol and 5.0 grams of 75% active sodium dioctylsulfosuccinate emulsifier (trade name: Aerosol™ OT). These components were mixed before use.

With the temperature of the water at 80° C., a polymer seed (Stage 1) was prepared by adding 50 grams of the monomer mixture to the flask followed by 10 millilitres of a 2 wt % solution of potassium persulfate in deionised water. Following a slight exotherm, the reaction proceeded for thirty minutes until the temperature returned to 80° C.

The core was then grown over the polymer seed particles (Stage 2) by firstly adding 20 millilitres of a 2 wt % solution of potassium persulfate in deionised water to the flask followed by continuous addition of 350 grams of the monomer mixture over approximately 35 minutes using a peristaltic pump. The reaction proceeded for a further fifteen minutes after the completion of the monomer mixture addition until the temperature returns to 80° C.

14.0 grams of 75% active dibenzoyl peroxide were dissolved in the remaining 100 grams of monomer mixture. This produces a residual dibenzoyl peroxide (BPO) content of approximately 2 wt % in the polymer.

The BPO-containing shell was then grown over the core (Stage 3) by firstly adding five millilitres of a 2 wt % solution of potassium persulfate in deionised water to the flask followed by continuous addition of the monomer mixture containing added BPO over approximately 10 minutes using a peristaltic pump. The reaction proceeded for a further fifteen minutes after all the monomer mixture had been added until the temperature has returned to 80° C.

The resultant dispersion was then cooled to below 40° C. and filtered through a 150 micron screen.

The acrylic polymer dispersion had a solids content of 25 wt %, reduced viscosity of 2.02 dl/g, Brookfield viscosity of 150 cPs, residual dibenzoyl peroxide of 1.90 wt % and a z-average dispersion particle size of 197 nm.

Example 1

Preparation of Acrylic Polymer Beads and Addition of Emulsion Polymer Coating

The aqueous phase of a suspension polymerization was prepared by adding 1750 millilitres of deionized water and 8 grams of hydroxyethyl cellulose powder (Natrosol HEC 250HR from Aqualon Ltd) to a 5 litre glass flask fitted with a stainless steel anchor-type stirrer. The flask contents were stirred at 400 rpm and heated to 40° C. to dissolve the hydroxyethyl cellulose. The organic phase containing 1,000 grams methyl methacrylate and 44.0 grams of 75% active dibenzoyl peroxide was then added, the stirrer speed adjusted to 650 rpm and the contents of the reactor flask heated to 77-80° C. using a water bath. The polymerization was continued at 77-80° C. until the reactor contents experienced an exotherm, typically to approximately 92-95° C. The reactor flask contents were then cooled to room temperature.

Application of an emulsion polymer coating to these beads was carried out as follows: 820 grams of the acrylic polymer bead slurry was added to a 5 litre glass flask fitted with a stainless steel anchor-type stirrer, followed by 200 gram of deionized water and 20 grams of aluminium sulfate. The mixture was then heated to 85° C. with stirring at 300 rpm. After the aluminium sulfate had dissolved, 84 grams of the final acrylic dispersion prepared in preparative example 1 were added dropwise over 20 minutes. The mixture was stirred at 300 rpm at 85° C. for a further 60 minutes before cooling the mixture to room temperature. The resultant polymer beads with coagulated emulsion polymer coating were then filtered, washed with deionized water, dried in an air circulating oven at 50° C. and screened through an 840 microns screen. The dried product was a free flowing polymer with mean particle size 95 microns

Example 2

Example 1 was repeated except that 30 grams of aluminium sulfate and 167 grams of the acrylic polymer dispersion of preparative example 1 were used.

The dried polymer beads with coagulated emulsion polymer coating had the consistency of a free flowing powder with mean particle size 110 microns.

Example 3

Example 1 was repeated except that 30 grams of aluminium sulfate and 225 grams of the acrylic polymer dispersion of preparative example 1 were used.

The dried polymer beads with coagulated emulsion polymer coating had the consistency of a free flowing powder with mean particle size 104 microns.

Example 4

Example 1 was repeated except that 167 grams of the acrylic polymer dispersion of preparative example 2 were used. The dried polymer beads with coagulated emulsion polymer coating had the consistency of a free flowing powder with mean particle size 96 microns.

Comparative Example 1

Preparation of Uncoated Polymer Bead

The polymer beads were made in the same way as example 1, but the application of an emulsion polymer coating was omitted. Analysis of the uncoated polymer beads gave the following results: mean particle size 68 μm, residual benzoyl peroxide content 3.0 wt %, weight average molecular weight (Mw) of 250 daltons and reduced viscosity 2.00 dl/g.

Comparative Example 2 and Examples 5 to 8

Preparation of Powder/Liquid Mixtures and Determination of Dough, Work and Set Times These examples involved the mixing of the powders from comparative example 1 and examples 1, 2, 3 and 4 with monomer liquid to determine the dough, work and set times of each powder/liquid mixture. The monomer liquid consisted of 99 parts by weight of MMA monomer containing 60ppm HQ inhibitor and 1 part by weight of N,N-dimethyl-p-toluidine (DMPT) accelerator. The mix ratio was 10.5 g polymer powder to 6 ml monomer liquid. The two components were firstly equilibrated in an incubator at 23° C. for at least 10 hours. The required amount of polymer powder was then placed into a polypropylene beaker, followed by the monomer liquid. Timing was started from the point of adding the powder to the liquid. Hand mixing was then carried out for 30 seconds using a metal spatula, whereupon the material was covered and left to stand. Periodically, the material was assessed and the dough, work and set times were recorded. Table 1 records the results.

It can be seen that the effect of the emulsion polymer coating in examples 5 to 8 significantly shortens the dough time compared to comparative example 2, thereby allowing an appreciable increase in work time.

TABLE 1

| | Example: | | | | |
|---|---|---|---|---|---|
| | Comparative example 2 | Example 5 | Example 6 | Example 7 | Example 8 |
| Identity of powder component: | Comparative example 1 (no emulsion polymer coating) | Example 1 | Example 2 | Example 3 | Example 4 |
| Dough time (minutes:seconds) | 15 | 7 | 1:30 | 1 | 1:30 |
| Work time (minutes:seconds) | 4 | 17 | 14 | 9:30 | 10:30 |
| Set time (minutes:seconds) | 22 | 28 | 18 | 13 | 18:30 |

Comparative Example 3 and Examples 9 and 10

Blends of Uncoated and Emulsion Polymer Coated Polymer Beads

To demonstrate how the dough, work and set times can be fine-tuned, powder blends of the uncoated beads of comparative example 1 with the emulsion polymer coated beads of example 3 were prepared in ratios 100:0, 50:50 and 25:75 wt % of comparative example 1: example 3. These blends were prepared by weighing out the relevant amount of each ingredient into a 150 gram capacity lab scale cone blender and then blending for 10 minutes. The resulting blends were then used to determine dough, work and set times as follows:

A monomer liquid was prepared consisting of 99 parts by weight of MMA monomer containing 60 ppm HQ inhibitor and 1 part by weight of N,N-dimethyl-p-toluidine (DMPT) accelerator. This was mixed with each polymer powder in mix ratio was 10.5 g polymer powder to 6 ml monomer liquid. The two components were firstly equilibrated in an incubator at 23° C. for at least 10 hours. The required amount of polymer powder was then placed into a polypropylene beaker, followed by the monomer liquid. Timing was started from the point of adding the powder to the liquid. Hand mixing was then carried out for 30 seconds using a metal spatula, whereupon the material was covered and left to stand. Periodically, the material was assessed and the dough, work and set times were recorded. Table 2 records the results.

It can be seen that the effect of incorporating the emulsion polymer coated polymer beads of example 3 into a powder blend (examples 9 and 10) is to significantly shorten the dough time compared to comparative example 3 that does not contain any emulsion polymer coated polymer beads, thereby allowing an appreciable increase in work time.

TABLE 2

|  | Comparative example 3 | Example 9 | Example 10 |
|---|---|---|---|
| Blend composition | 100:0 wt % Comparative example 1:Example 3 | 50:50 wt % Comparative example 1:Example 3 | 25:75 wt % Comparative example 1:Example 3 |
| Dough time (minutes:seconds) | 15 | 8:00 | 1:30 |
| Work time (minutes:seconds) | 4 | 10 | 12 |
| Set time (minutes:seconds) | 22 | 21 | 16 |

Comparative Example 4 and Examples 11 and 12

Blends of Uncoated and Emulsion Polymer Coated Polymer Beads with Radiopacifier (Zirconium Oxide)

The effect of adding radiopacifier to the polymer powders was assessed. The radiopacifier selected was zirconium (IV) oxide (available from Sigma-Aldrich as 5 um powder, product code 230693) and this was blended with the uncoated beads of comparative example 1 and the emulsion polymer coated polymer beads of examples 3 or 4 in the ratio 20:80 wt % zirconium oxide:polymer powder. These blends were prepared by weighing out the relevant amount of each ingredient into a 150 gram capacity lab scale cone blender and then blending for 10 minutes. The resulting blends were then used to determine dough, work and set times as follows: A monomer liquid was prepared consisting of 99 parts by weight of MMA monomer containing 60 ppm HQ inhibitor and 1 part by weight of N,N-dimethyl-p-toluidine (DMPT) accelerator. This was mixed with each polymer powder in mix ratio was 10.5 g polymer powder to 6 ml monomer liquid. The two components were firstly equilibrated in an incubator at 23° C. for at least 10 hours. The required amount of polymer powder was then placed into a polypropylene beaker, followed by the monomer liquid. Timing was started from the point of adding the powder to the liquid. Hand mixing was then carried out for 30 seconds using a metal spatula, whereupon the material was covered and left to stand. Periodically, the material was assessed and the dough, work and set times were recorded. Table 3 records the results.

It can be seen that, even in the presence of zirconium oxide radiopacifier, the effect of the emulsion polymer coating in examples 13 to 14 significantly shortens the dough time compared to comparative example 4, thereby allowing an appreciable increase in work time.

TABLE 3

|  | Comparative example 4 | Example 11 | Example 12 |
|---|---|---|---|
| Blend composition | 20:80 wt % zirconium oxide:comparative example 1 | 20:80 wt % zirconium oxide:example 3 | 20:80 wt % zirconium oxide:example 4 |
| Dough time (minutes:seconds) | 17 | 1 | 9 |
| Work time (minutes:seconds) | 6:30 | 10 | 13 |
| Set time (minutes:seconds) | 25 | 14:30 | 27:30 |

Figure 1:
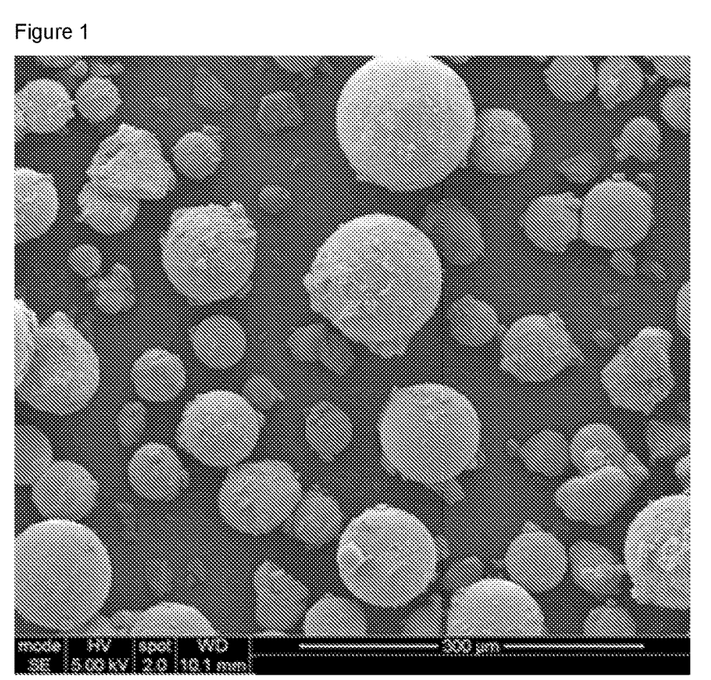
FIG. 1 shows an SEM image of the surface of coated acrylic polymer beads according to the invention.
Figure 2:
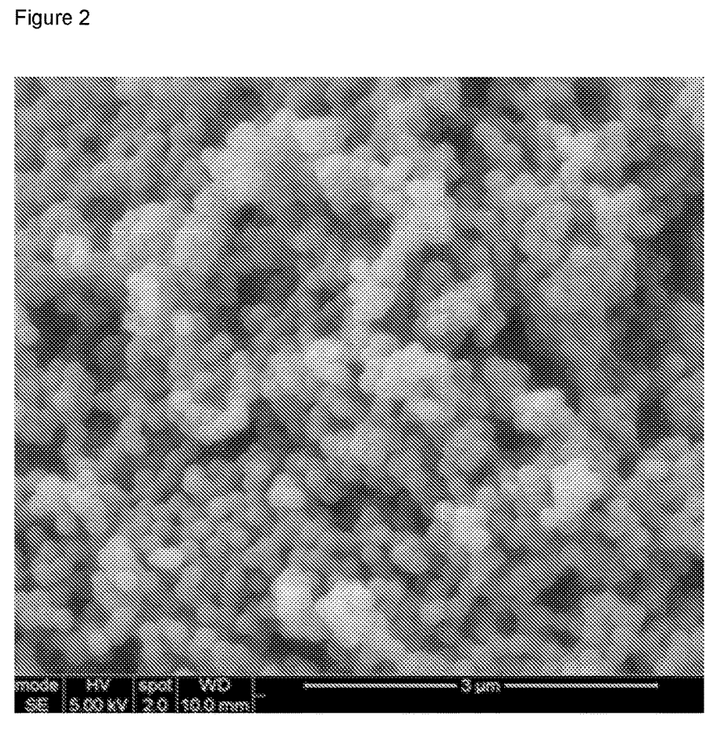
FIG. 2 shows an SEM image of the emulsion polymerized microparticles on the surface of the coated acrylic polymer beads according to the invention at a higher magnification than the image of FIG. 1.

Scanning Electron Microscopy (SEM) Examination of Emulsion Polymer Coated Polymer Beads The product of example 4 was examined by SEM imaging to show the morphology of the dried polymer beads with coagulated emulsion polymer coating.

FIG. 1 (300 micron scale bar) shows that the coagulated emulsion polymer particles (ca. 0.2 micron diameter) are mainly coating the polymer beads.

FIG. 2 (3 micron scale bar) shows that the emulsion polymer particles are coagulated together to form a microporous morphology.

Scanning Electron Microscopy (SEM) Examination of Uncoated Polymer Beads

Figure 3:
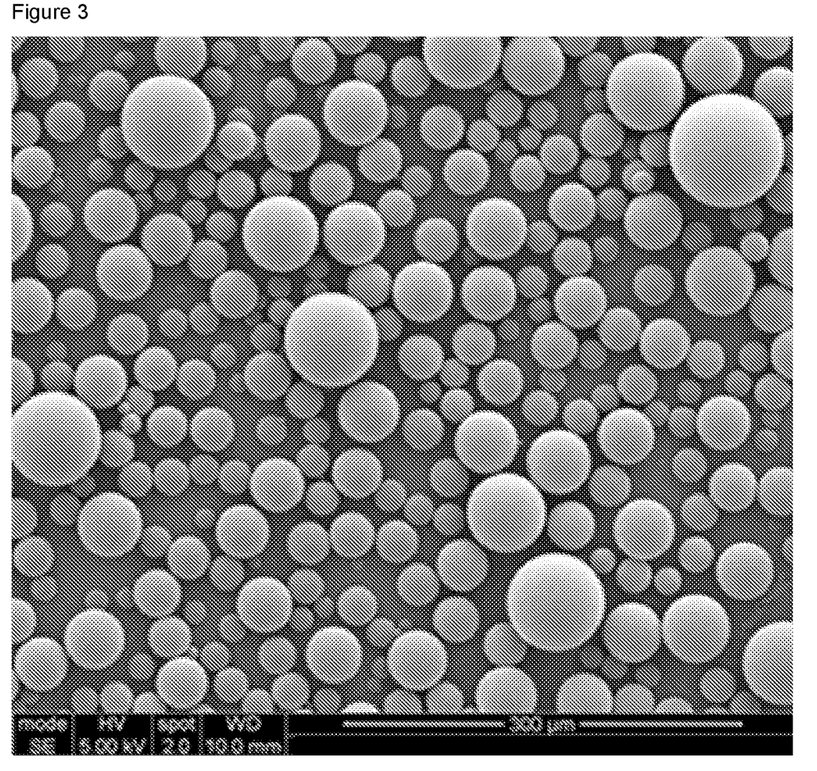
FIG. 3 shows an SEM view of the surface of acrylic polymer beads without an emulsion polymerized microparticle coating.

The product of comparative example 1 was also examined by SEM imaging to show the morphology of the dried polymer beads without an emulsion polymer coating. FIG. 3 shows that the beads are devoid of structure and have a smooth surface.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:
1. A composition comprising coated acrylic polymer beads comprising:
    a) an acrylic bead polymer core produced by suspension polymerisation and having a Tg of >70° C.; and b) emulsion polymerised acrylic microparticles at least partially coating the surface of the said acrylic bead polymer core;

wherein the emulsion polymerized acrylic microparticles (b) reduce the dough time of the acrylic bead polymer core (a) when the polymer beads are combined with an acrylic monomer and an initiator;

wherein at least 5% of the bead polymer core surface is coated with the said microparticles wherein the Z-average particle size range for the emulsion polymerized microparticles is between 0.02-1 μm, and wherein the mean particle size of the bead polymer cores is in the range 2-150 μm.

2. A composition comprising coated acrylic polymer beads comprising:

a) an acrylic bead polymer core produced by suspension polymerisation; and b) emulsion polymerised acrylic microparticles at least partially coating the surface of the said acrylic bead polymer core wherein the microparticles form a porous coalesced network;

wherein the emulsion polymerized acrylic microparticles (b) reduce the dough time of the acrylic bead polymer core (a) when the polymer beads are combined with an acrylic monomer and an initiator;

wherein at least 5% of the bead polymer core surface is coated with the said microparticles wherein the Z-average particle size range for the emulsion polymerized microparticles is between 0.02-1 μm, and wherein the mean particle size of the bead polymer cores is in the range 2-150 μm.

3. The composition according to claim 1, wherein the microparticles form a porous coalesced network.

4. The composition according to claim 2, wherein the acrylic bead polymer core produced by suspension polymerisation has a Tg of >70° C.

5. The composition according to claim 1, wherein at least 10% of the bead polymer core surface is coated with the said microparticles.

6. The composition according to claim 1, wherein the composition is a multi-part composition and further comprises an acrylic monomer and an initiator wherein the acrylic monomer component and the initiator component are located in separate parts of the multi-part composition so that the monomer component is storage stable to polymerization; and wherein, upon mixing the coated acrylic polymer beads with both the liquid acrylic monomer and initiator, the composition hardens to a solid mass and forms a cement.

7. The composition according to claim 6, wherein the coated microparticles form a porous coalesced network of microparticles on the surface of the core.

8. The composition according to claim 1, wherein the coated acrylic polymer beads are solid.

9. The composition according to claim 1, wherein the ratio of emulsion polymerized microparticles (b) to suspension polymerized beads (a) is between 1:99 to 50:50 w/w.

10. The composition according to claim 1, wherein the acrylic polymer bead (a) or emulsion polymerized microparticle (b) are independently homopolymers of a polyalkyl (alk)acrylate, homopolymers or (alk)acrylic acid, or copolymers of an alkyl(alk)acrylate or (alk)acrylic acid with one or more other vinyl monomers in which at least 50% of the monomer residues are acrylic monomer residues.

11. The composition according to claim 1, wherein independently the acrylic polymer bead (a) or the emulsion polymerized microparticle is made of a homopolymer of methyl methacrylate or a copolymer of methyl methacrylate with one or more other vinyl monomers.

12. The composition according to claim 6, wherein the acrylic monomer is liquid and is an alkyl(alk)acrylate or an (alk)acrylic acid, optionally further comprising one or more additional comonomers.

13. The composition according to claim 6, wherein the multi-part composition is a bone cement forming composition, a dental composition or a composition for medical implantation.

14. The composition according to claim 13, wherein the composition is a bone cement forming composition.

15. The composition according to claim 11, wherein the one or more other vinyl monomers are present and are styrene or methyl acrylate.

16. The composition according to claim 12, wherein the comonomers are styrene and methyl acrylate.

17. The composition according to claim 6, further comprising an additive selected from the group consisting of a catalyst, a radiopacifying filler, a dyestuff, and a filler.

18. The composition according to claim 6, further comprising an accelerator, activator, or stabilizer.

19. A method of making the composition of claim 1, comprising:

a) providing acrylic polymer bead particles prepared by suspension polymerization;

b) providing emulsion polymerized microparticles in the form of a dispersion, c) mixing the suspension of a) and dispersion of b) in the presence of an electrolyte to cause coagulation of the emulsion microparticles with the bead particles to form an acrylic bead polymer core at least partially coated with emulsion polymerised acrylic microparticles.

20. The method according to claim 19, wherein the ratio of emulsion polymerized microparticle dispersion to suspension polymerized bead particles is between 2:98 to 60:40 w/w thereof.

21. A method of producing an acrylic cement comprising:

(a) providing coated acrylic polymer beads comprising
(1) an acrylic bead polymer core produced by suspension polymerisation and having a Tg of >70° C.; and
(2) emulsion polymerised acrylic microparticles at least partially coating the surface of the said acrylic bead polymer core;

the coating being effective to reduce the dough time when the polymer beads are combined with an acrylic monomer and an initiator; and wherein at least 5% of the bead polymer core surface is coated with the said microparticles wherein the Z-average particle size range for the emulsion polymerized microparticles is between 0.02-1 μm, and wherein the mean particle size of the bead polymer cores is in the range 2-150 μm, (b) providing a liquid acrylic monomer, (c) providing an initiator d) mixing the coated polymer beads (a) the liquid monomer (b), and the initiator (c) to make a dough, e) optionally, placing the dough in a mould or body cavity or around an implant by hand manipulation or injection, and f) allowing the dough to set and harden to a solid mass.

* * * * *

UNITED STATES PATENT AND TRADEMARK OFFICE
CERTIFICATE OF CORRECTION

PATENT NO. : 11,548,966 B2
APPLICATION NO. : 16/763502
DATED : January 10, 2023
INVENTOR(S) : Michael Stephen Chisholm Page 1 of 1

It is certified that error appears in the above-identified patent and that said Letters Patent is hereby corrected as shown below:

On the Title Page (30) Foreign Application Priority Data: Please correct "1719227" to read --1719227.9--

(56) References Cited, OTHER PUBLICATIONS, Page 2, Column 2, Line 30: Please correct "2018300870256" to read --2018800870256--

In the Claims

Column 27, Line 11, Claim 1: Please correct "0.02-1_µm" to read --0.02-1 µm--

Column 27, Line 29, Claim 2: Please correct "0.02-1_µm" to read --0.02-1 µm--

Signed and Sealed this
Eighteenth Day of April, 2023

Katherine Kelly Vidal
*Director of the United States Patent and Trademark Office*